(12) United States Patent
Iwanaga et al.

(10) Patent No.: US 7,320,519 B2
(45) Date of Patent: Jan. 22, 2008

(54) OPHTHALMIC APPARATUS

(75) Inventors: Tomoyuki Iwanaga, Yokohama (JP); Hiroshi Itoh, Yokohama (JP); Shinya Tanaka, Shinagawa-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/680,951

(22) Filed: Mar. 1, 2007

(65) Prior Publication Data

US 2007/0242222 A1    Oct. 18, 2007

(30) Foreign Application Priority Data

Apr. 4, 2006    (JP) .............................. 2006-102718

(51) Int. Cl.
*A61B 3/10* (2006.01)
(52) U.S. Cl. ..................................... 351/221
(58) Field of Classification Search ............... 351/221, 351/200, 211, 204, 205, 206, 208
See application file for complete search history.

(56) References Cited

U.S. PATENT DOCUMENTS 6,636,696 B2 * 10/2003 Saito ........................... 396/18
7,029,120 B2 *  4/2006 Kushida ..................... 351/211

FOREIGN PATENT DOCUMENTS

| JP | 10-192244 A | 7/1998 |
| JP | 11-225970 A | 8/1999 |

* cited by examiner

*Primary Examiner*—Ricky Mack
*Assistant Examiner*—Tuyen Tra
(74) *Attorney, Agent, or Firm*—Canon USA Inc IP Division

(57) ABSTRACT

An ophthalmic apparatus allows a fixation-target projecting unit for fundus observation to project a fixation target for fundus observation onto a position not coinciding with a center of a light path of an observation optical system but corresponding to a position to which a fixation target for anterior-ocular-observation is projected. Thus, it is not necessary for an operator to perform positioning and fixation guiding operations again, thereby contributing to a shorter imaging time and less complexity and trouble in the overall operation.

2 Claims, 6 Drawing Sheets

OPHTHALMIC APPARATUS

BACKGROUND OF THE INVENTION

1. Field of the Invention

The present invention relates to an ophthalmic apparatus used at, for example, an eye clinic for picking up an image of a fundus of a subject's eye.

2. Description of the Related Art

In conventional ophthalmic apparatuses, an optical system that is separate from an image-pickup optical system is provided for the purpose of facilitating the positioning between the apparatus and the subject's eye. A target member, which serves as a fixation target, is disposed within that optical system at a position where the target member is in a conjugate relationship with the fundus of the subject's eye. The target member is illuminated from the back so that the target thereof can be projected onto the fundus of the subject's eye.

Japanese Patent Laid-Open No. 10-192244 discloses an ophthalmic apparatus which includes an optical member and an anterior-ocular-observation optical system disposed in a removable manner. The optical member has a scattering-reflecting area, serving as a fixation target for anterior-ocular observation, in at least one section of a surface thereof that is distant from the subject's eye. The anterior-ocular-observation optical system has a light source configured to illuminate the optical member from the side.

Japanese Patent Laid-Open No. 11-225970 discloses an improved version of the ophthalmic apparatus of Japanese Patent Laid-Open No. 10-192244. In detail, this ophthalmic apparatus includes a fixation target member for anterior-ocular-observation formed by using a luminous coating material, a switching unit configured to move the fixation target member onto a light path or to remove the fixation target member from the light path, and an illuminating unit configured to illuminate the fixation target member when the fixation target member is removed from the light path.

In the ophthalmic apparatus according to Japanese Patent Laid-Open No. 11-225970, in order to simplify the structure of the apparatus, the optical member having its scattering-reflecting area set on a fundus-conjugate plane of an observation/image-pickup optical system at the time of anterior-ocular observation is disposed in a removable manner together with a lens group used for anterior-ocular observation. By illuminating the optical member from the side, the light from the scattering-reflecting area can be projected onto the subject's eye as a fixation target. In this apparatus, the optical member having the scattering-reflecting area is provided within the anterior-ocular-observation lens group and is used as a fixation target member for anterior-ocular observation.

However, in the conventional examples described above, when the anterior-ocular-observation lens group is removed from the light path to switch from an anterior-ocular observation mode to a fundus observation mode, the position of the fixation target for anterior-ocular-observation projected on the subject's eye differs from the position of the fixation target for fundus observation projected on the subject's eye. This implies that the visual line direction of the subject's eye changes in response to the switching operation. Therefore, even if the positioning between the subject's eye and the apparatus is adjusted for the anterior-ocular observation mode, the positioning process will need to be performed again for the fundus observation mode.

Normally, for a screening test, such as a mass health examination, a fundus image in which the optic disc and the macula lutea are evenly disposed is captured. For this reason, if the visual line changes upon switching to the fundus observation mode, the fixation of the subject's eye needs to be guided again, thus leading to a troublesome and complex operation. In addition, if the fixation target for fundus observation is preliminarily disposed at a position suitable for a certain kind of examination, the subject may possibly lose sight of the fixation target since the fixation target will suddenly be switched to another one upon switching from the anterior-ocular observation mode to the fundus observation mode.

The present invention provides an ophthalmic apparatus that prevents the subject from losing sight of a fixation target even in the case of switching between the anterior-ocular observation mode and the fundus observation mode.

SUMMARY OF THE INVENTION

According to an aspect of the present invention, an ophthalmic apparatus is provided, which prevents the subject from losing sight of a fixation target even in the case of switching between the anterior-ocular observation mode and the fundus observation mode. More specifically, the ophthalmic apparatus includes a first optical system for observing a subject's illuminated eye, a second optical system for changing an observation area through the first optical system, the second optical system being moved into a light path of the first optical system when an anterior-ocular image of the subject's eye is to be observed, the second optical system being removed from the light path of the first optical system when a fundus of the subject's eye is to be observed, a first fixation-target projecting unit for anterior-ocular observation within the second optical system and configured to project fixation targets for anterior-ocular observation onto the subject's eye at positions not coinciding with a center of the light path, a second fixation-target projecting unit for fundus observation configured to project fixation targets for fundus observation onto the subject's eye, and a controller that allows the second fixation-target projecting unit to project the fixation targets for fundus observation onto predetermined positions on the subject's eye when the second optical system is removed, the predetermined positions corresponding to the positions to which the fixation targets for anterior-ocular observation are projected.

Further features of the present invention will become apparent from the following description of exemplary embodiments with reference to the attached drawings.

DESCRIPTION OF THE EMBODIMENTS

Exemplary embodiments of the present invention will now be described with reference to the drawings.

First Exemplary Embodiment

Figure 1:
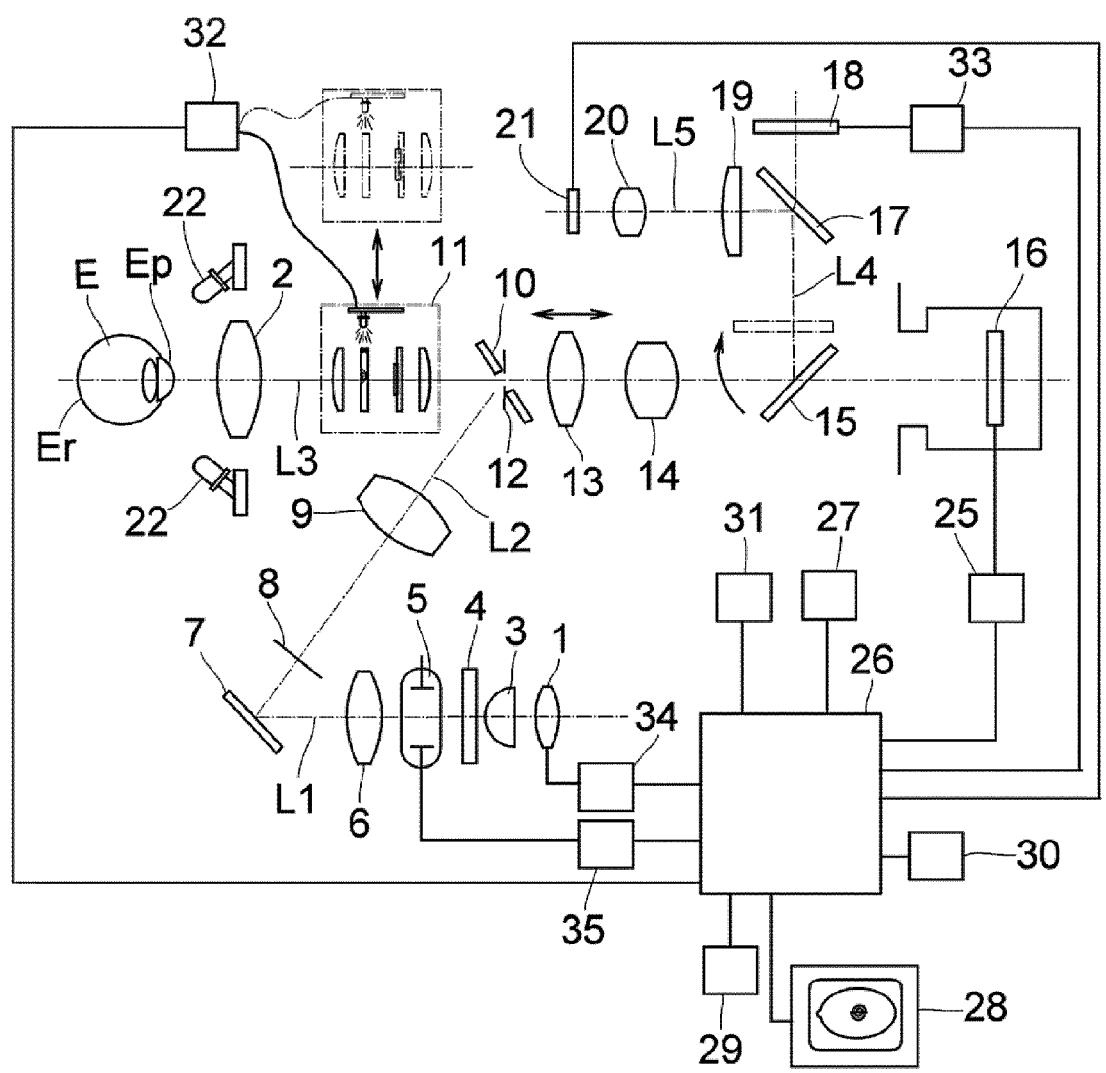
FIG. 1 schematically illustrates a fundus camera.

FIG. 1 schematically illustrates a fundus camera serving as an ophthalmic apparatus according to a first exemplary embodiment of the present invention. The fundus camera includes a condenser lens 3, a filter 4 that transmits infrared light but blocks visible light, a light source 5 for picking up an image which is defined by, for example, a strobe light, a lens 6, and a mirror 7. These components are arranged on a light axis L1 of a light path that extends from an observation light source 1 for emitting fixed light, such as a halogen lamp, to an objective lens 2.

The fundus camera also includes a ring stop 8 having a ring-shaped aperture, a relay lens 9, and a perforated mirror 10 having an aperture in the center thereof, which are arranged in that order on a light axis L2 extending in the reflecting direction of the mirror 7. The fundus camera further includes an anterior-ocular observation optical system 11 disposed in a removable manner on a light axis L3 extending in the reflecting direction of the perforated mirror 10, and the objective lens 2 which is fixed on the light axis L3. The anterior-ocular observation optical system 11 is an optical system for changing an observation area. The anterior-ocular observation optical system 11 is moved onto the light axis L3 when an image of an anterior ocular segment Ep of a subject's eye E is to be observed, but is removed from the light axis L3 when an image of a fundus Er of the subject's eye E is to be observed. This operation is controlled by a controller 26 on the basis of a selection made by an observation-area selecting switch 29.

The aperture of the perforated mirror 10 has a stop 12 disposed therein. Behind the stop 12 on the light axis L3 are a focusing lens 13 that moves for focus adjustment, a lens 14, a flip-up mirror 15, and a image pickup element 16 arranged in that order.

A dichroic mirror 17 that reflects infrared light but transmits visible light, and a fixation target member 18 for fundus observation are arranged on a light axis L4 extending in the reflecting direction of the flip-up mirror 15. The fixation target member 18 includes a liquid crystal display panel and a backlight configured to project a fixation target onto a desired position on the fundus Er of the subject's eye E. The fixation target member 18 is disposed at a position where it is optically conjugate with the image pickup element 16. A field lens 19, a lens 20, and an image pickup element for observation 21 are arranged in that order on a light axis L5 extending in the reflecting direction of the dichroic mirror 17. The light axes L3, L4, and L5 are all disposed in the center of an observation light path.

Furthermore, an anterior-ocular illuminating light source 22 is disposed near the objective lens 2 such as to illuminate the anterior ocular segment of the subject's eye E.

An output of the image pickup element 16 for picking up a still image for storing is connected to the controller 26 via an image processor 25. The controller 26 controls the entire apparatus and is connected to the image pickup element for observation 21, an image memory 27, a monitor 28, the observation-area selecting switch 29 for selecting the anterior ocular segment or the fundus of the subject's eye E as an observation area, and a switch 30 for picking up an image. Furthermore, the controller 26 is also connected to a left/right eye detector 31 configured to determine whether the subject's eye E is a left eye or a right eye. This determination by the left/right eye detector 31 is based on a detection by a micro-switch (not shown) or the like for detecting the horizontal position of a stage mechanism, which holds the optical portion of the apparatus and is movable in the forward, backward, horizontal, and vertical directions with respect to the subject's eye E.

An output of the controller 26 is connected to a fixation-target light-source controller 32 configured to control a fixation target for anterior-ocular-observation within the anterior-ocular observation optical system 11, and also to a controller 33 configured to control the fixation target member 18 for fundus observation. Moreover, the output of the controller 26 is also connected to an observation-light-source controller 34 configured to control the observation light source 1, a light-source controller 35 configured to control the light source 5, and a controller (not shown) configured to control the anterior-ocular illuminating light source 22.

Figure 2:
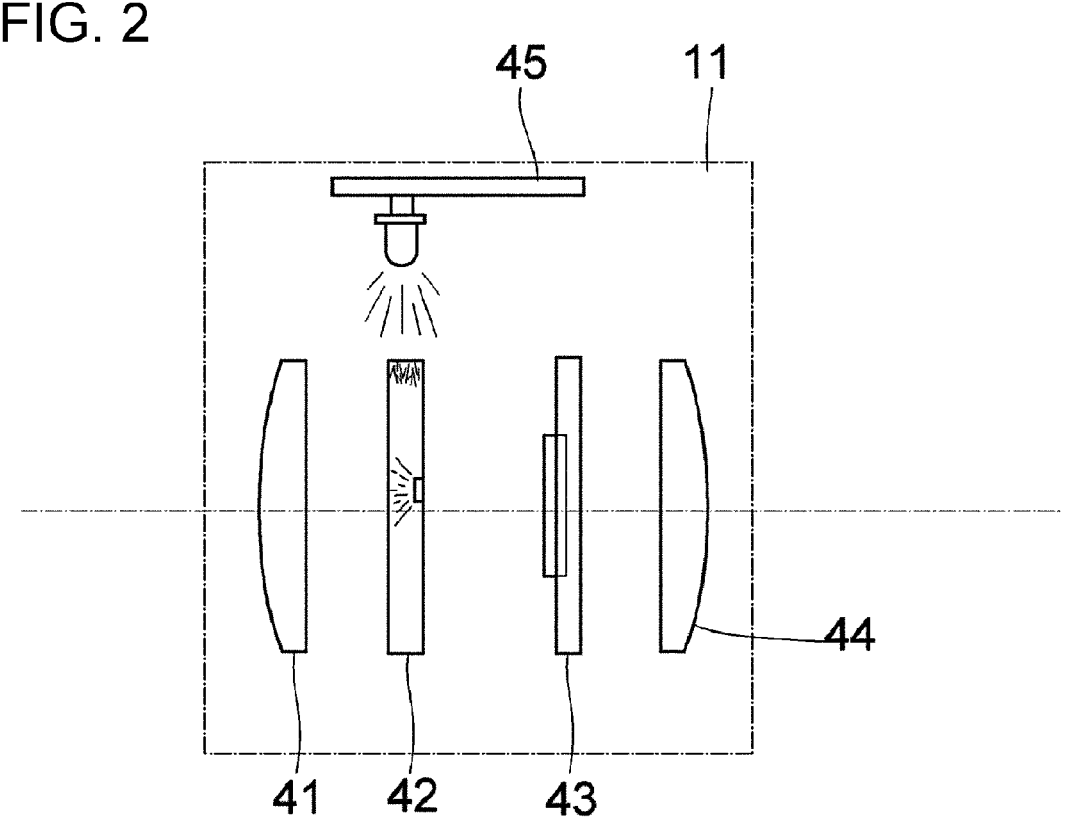
FIG. 2 is an enlarged cross-sectional view of an anterior-ocular observation optical system.

FIG. 2 is an enlarged cross-sectional view of the anterior-ocular observation optical system 11. The anterior-ocular observation optical system 11 contains a target member 42, a prism 43 having an image splitting prism component in the center thereof, and a lens 44 arranged in that order on a light path of a lens 41. Moreover, a target-illuminating light source 45 configured to illuminate the target member 42 from the side is disposed in the vicinity of the target member 42. These components are integrally removable with respect to the light axis L3.

Figure 3:
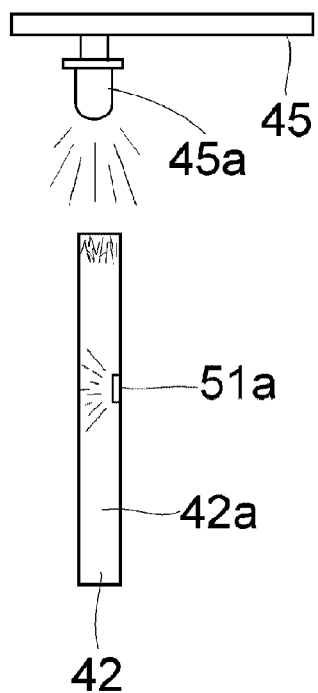
FIG. 3 is a side view of a target member and a target-illuminating light source according to a first embodiment of the present invention.
Figure 4:
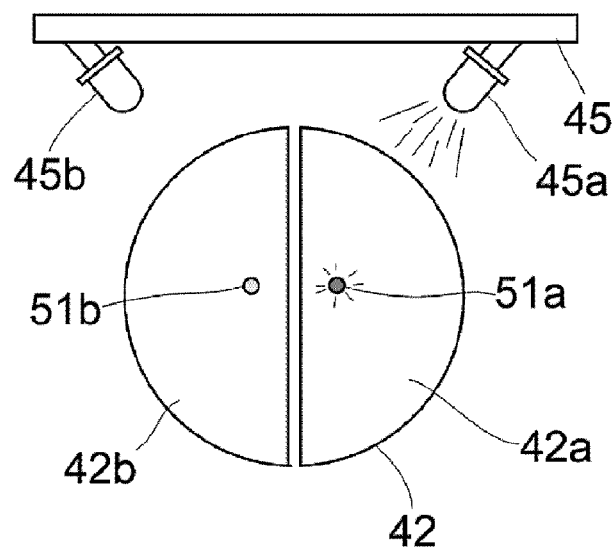
FIG. 4 is a front view of the target member and the target-illuminating light source in the first embodiment, as viewed from a subject's eye.

FIG. 3 is a side view of the target member 42 and the target-illuminating light source 45, and FIG. 4 is a front view as viewed from the subject's eye E. The target member 42 includes two semicircular transparent optical components 42a and 42b whose peripheral edges serve as scattering surfaces. The optical components 42a and 42b respectively have fixation targets 51a and 51b used for anterior-ocular observation.

The fixation targets 51a and 51b are each formed by eroding a section of the corresponding optical component into a predetermined target shape with an agent and then filling the eroded section with a white coating material, which serves as a scattering material. Furthermore, when placed on the light axis L3, the fixation targets 51a and 51b are set at positions where they are in a substantially conjugate relationship with the fundus Er of the subject's eye E with respect to the objective lens 2 and the lens 41. The prism 43 in the anterior-ocular observation optical system 11 is set at a position where it is in a substantially conjugate relationship with the anterior ocular segment Ep of the subject's eye E with respect to the objective lens 2 and the lens 41 when the operating distance between the subject's eye E and the objective lens 2 is appropriate.

The target-illuminating light source 45 includes two light emitting diodes (LEDs) 45a and 45b. The LED 45a illuminates the fixation target 51a of the target member 42, whereas the LED 45b illuminates the fixation target 51b. Moreover, the target-illuminating light source 45 is connected to an output of the fixation-target light-source controller 32 which selectively turns on the LEDs 45a and 45b.

When a power switch (not shown) is turned on, the controller 26 moves the anterior-ocular observation optical system 11 onto the light axis L3 and turns on the anterior-ocular illuminating light source 22. Furthermore, based on the left/right-eye detection result by the left/right eye detector 31, the controller 26 controls the fixation-target light-source controller 32 so as to turn on the LED 45a or the LED 45b, thereby illuminating the corresponding one of the fixation targets 51a and 51b.

For example, if the left/right eye detector 31 detects that the subject's eye E is a right eye, the LED 45a is turned on. A light beam emitted from the LED 45a enters the optical component 42a through the peripheral edge thereof and is repetitively scattered within the optical component 42a, thereby illuminating the fixation target 51a for anterior-ocular observation. The light beam illuminating the fixation target 51a is scattered and is substantially collimated by the lens 41 and the objective lens 2 before reaching the subject's eye E. The subject's gaze is fixed on the image of the fixation target 51a for anterior-ocular-observation through the objective lens 2 and the lens 41, whereby the visual line of the subject is stabilized. Subsequently, the examiner can observe the anterior ocular segment Ep of the subject's eye E to check for cataracts or the like.

The light emitted from the anterior-ocular illuminating light source 22 illuminates the anterior ocular segment Ep of the subject's eye E. The light reflected by the anterior ocular segment Ep travels through the objective lens 2, the anterior-ocular observation optical system 11, the stop 12, the focusing lens 13, and the lens 14, and is then reflected by the flip-up mirror 15 in the direction of the light axis L4. Subsequently, the light is reflected by the dichroic mirror 17 in the direction of the light axis L5, and then travels through the field lens 19 and the lens 20 so as to form an image on the image pickup element for observation 21. The controller 26 displays the image picked up by the image pickup element for observation 21 on the monitor 28.

While observing the image of the anterior ocular segment Ep of the subject's eye E displayed on the monitor 28, the examiner can operate an operating rod (not shown) to roughly adjust the positioning between the fundus camera and the subject's eye E. This positioning process can be performed readily since the visual line of the subject's eye E is stable.

Because the prism 43 in the anterior-ocular observation optical system 11 is disposed at a position where it is substantially optically conjugate with the image pickup element for observation 21, if the anterior ocular segment Ep is supposedly not in an optically conjugate relationship with the image pickup element for observation 21, the observation image of the anterior ocular segment Ep will unfavorably be observed in a state where the upper and lower portions of the image are split in the horizontal directions. In contrast, when the operating distance between the subject's eye E and the apparatus is appropriate, the anterior ocular segment Ep of the subject's eye E and the image pickup element for observation 21 are in an optically conjugate relationship with each other, whereby the image is observed as a single non-split image.

After completing the rough positioning process between the fundus camera and the subject's eye E, the examiner can press the observation-area selecting switch 29. Based on the detection of the selection made with the switch 29, the controller 26 controls an inserting-removing unit (not shown) so as to remove the anterior-ocular observation optical system 11 from the light axis L3. In addition, the controller 26 controls the controller 33 so as to drive the liquid crystal display panel and the backlight of the fixation target member 18 for fundus-observation.

Figure 5:
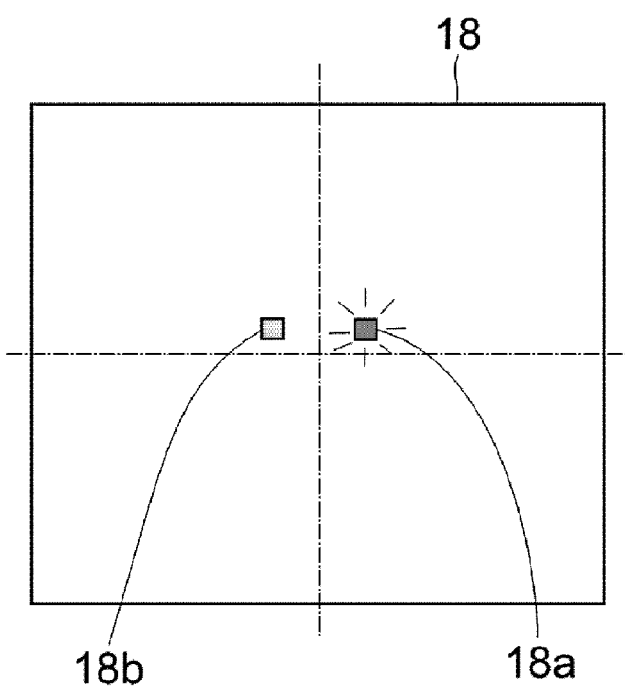
FIG. 5 illustrates a fixation target member for fundus observation.

Referring to FIG. 5, the fixation target member 18 includes a pair of fixation targets 18a and 18b for fundus of the left and right eyes. Based on the detection result by the left/right eye detector 31, the fixation target 18a for fundus observation, for example, is illuminated.

Moreover, the fixation target 18a for fundus observation is projected onto the fundus Er of the subject's eye E at the same position as the fixation target 51a, which had been projected prior to the removal of the anterior-ocular observation optical system 11.

A light beam output from the fixation target 18a for fundus observation is transmitted through the dichroic mirror 17 and is deflected by the flip-up mirror 15 in the direction of the light axis L3. The light beam then travels through the lens 14, the focusing lens 13, the stop 12, and the objective lens 2 so as to reach the fundus Er of the subject's eye E. The subject's gaze is fixed on the image of the fixation target 18a for fundus observation projected on the fundus Er, whereby the visual line can be stabilized.

Figure 6:
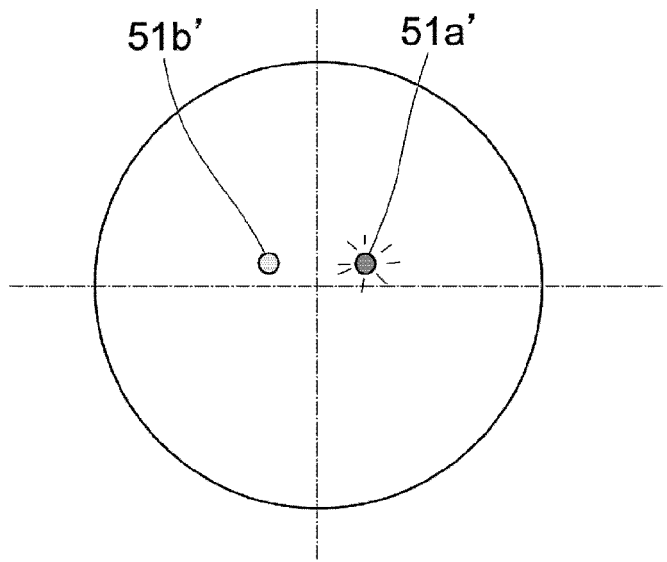
FIG. 6 illustrates a fixation-target image for anterior-ocular-observation observed by the subject's eye.
Figure 7:
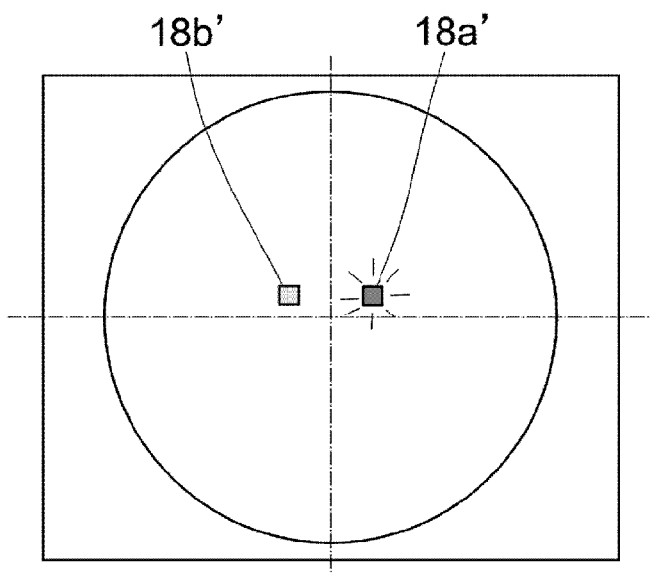
FIG. 7 illustrates a fixation-target image for fundus observation observed by the subject.

FIG. 6 illustrates a fixation-target image 51a' which is an image of the fixation target 51a for anterior-ocular-observation observed by the subject's eye E. FIG. 7 illustrates a fixation-target image 18a' which is an image of the fixation target 18a observed by the subject's eye E. The fixation-target image 51a' and the fixation-target image 18a' are projected in the same visual line direction as viewed from the subject's eye E. As a result, a visual line of the subject's eye E may be stabilized without losing track of the fixation target even if the observation area is switched from the anterior ocular segment Ep to the fundus Er by the insertion or the removal of the anterior-ocular observation optical system 11 with respect to the light axis L3 in response to the operation of the observation-area selecting switch 29. Moreover, the projected position of the fixation-target image 18a' does not coincide with the center of the observation light path. For example, referring to FIG. 8, the fixation-target image 18a' is projected onto a position where a fundus image suitable for a screening test, such as a complete physical examination and a mass health examination, can be attained. In such a suitable fundus image, an optic disc N and a macula lutea M are evenly disposed.

At the time of fundus observation, the controller 26 controls the observation-light-source controller 34 so as to turn on the observation light source 1. A light beam emitted from the observation light source 1 is condensed by the condenser lens 3. The filter 4 then transmits only the infrared light portion of the light beam while blocking the visible light portion thereof. The light beam passes through the light source 5 so as to enter the lens 6 and then the mirror 7. The light beam reflected by the mirror 7 is made into a ring-shaped light beam by passing through the ring stop 8, and then travels through the relay lens 9 to reach the perforated mirror 10 where the light beam is deflected in the direction of the light axis L3. Finally, the light beam passes through the objective lens 2 so as to illuminate the fundus Er of the subject's eye E.

The light beam incident on the fundus Er is reflected and scattered by the fundus Er. After traveling through the objective lens 2, the stop 12, the focusing lens 13, and the lens 14, the light beam is deflected by the flip-up mirror 15 and then by the dichroic mirror 17 in the direction of the light axis L5. Subsequently, the light beam travels through the field lens 19 and the lens 20 so as to form an image on the image pickup element for observation 21. Finally, the controller 26 displays the fundus image picked up by the image pickup element for observation 21 on the monitor 28.

While observing the fundus image displayed on the monitor 28, the examiner can finely adjust the positioning between the fundus camera and the subject's eye E, and can then rotate a focusing knob (not shown) to move the focusing lens 13 for a focusing operation. When the positioning and focusing operations are completed, the examiner can press the switch 30 for picking up the fundus image.

When the pressing of the switch 30 is detected, the controller 26 removes the flip-up mirror 15 from the light axis L3 and then controls the light-source controller 35 so that the light source 5 emits light in pulses. A light beam emitted from the light source 5 illuminates the fundus Er of the subject's eye E by traveling along the same path as the light beam emitted from the observation light source 1. The light beam is reflected and scattered by the fundus Er and travels through the objective lens 2, the stop 12, the focusing lens 13, and the lens 14 so as to form an image on the image pickup element 16. The image is finally picked up by the image pickup element 16.

The controller 26 controls the image processor 25 so as to perform an A/D conversion and predetermined image processing on the fundus image picked up by the image pickup element 16. Subsequently, the processed image is stored in the image memory 27 and is displayed on the monitor 28. At the same time, the controller 26 controls the inserting-removing unit (not shown) so as to move the anterior-ocular observation optical system 11 onto the light axis L3.

When the imaging of the right eye is completed, the examiner can operate the operating rod to shift the fundus camera towards the subject's left eye. Subsequently, the left/right eye detector 31 detects that the subject's eye E is a left eye. The controller 26 controls the fixation-target light-source controller 32 so as to turn on the LED 45$b$ to illuminate the fixation target 51$b$ for anterior-ocular observation. Thus, the fixation target 51$b$ for anterior-ocular-observation is projected onto the subject's eye E. The subject's eye's E gaze is fixed at a fixation-target image 51$b$', which is an image of the fixation target 51$b$ projected on the subject's eye E, whereby the visual line is stabilized.

Similar to the case of the right eye, after completing the rough positioning process between the fundus camera and the subject's eye E, the examiner can press the observation-area selecting switch 29. In response to the detection of the pressing of the observation-area selecting switch 29, the controller 26 removes the anterior-ocular observation optical system 11 from the light axis L3. In addition, based on the detection result by the left/right eye detector 31, the controller 26 controls the controller 33 so as to illuminate the fixation target 18$b$ for fundus observation. Accordingly, a fixation-target image 18$b$' for fundus observation is projected onto the subject's eye E.

The subject's eye's E gaze is fixed at the projected fixation-target image 18$b$' so that the visual line is stabilized. Similar to the case of the right eye, upon completion of the positioning and focusing operations for the left eye, the examiner can press the switch 30. In response to the detection of the pressing of the switch 30, the controller 26 stores a fundus image of the left eye in the image memory 27 and displays the image on the monitor 28. Furthermore, the controller 26 moves the anterior-ocular observation optical system 11 onto the light axis L3 again.

According to the present embodiment, the subject's eye E is prevented from losing sight of the fixation target even when the fixation target 51$a$ or 51$b$ for anterior-ocular observation is switched to the fixation target 18$a$ or 18$b$ for fundus observation. Consequently, since the visual line does not change, it is not necessary to readjust the positioning between the fundus camera and the subject's eye E. This contributes to a shorter imaging time and less complexity and trouble in the overall operation. For example, in mass health screening, a cataract examination which is based on anterior-ocular observation can be smoothly and successively switched to a glaucoma examination which is based on fundus observation.

Second Exemplary Embodiment

Figure 9:
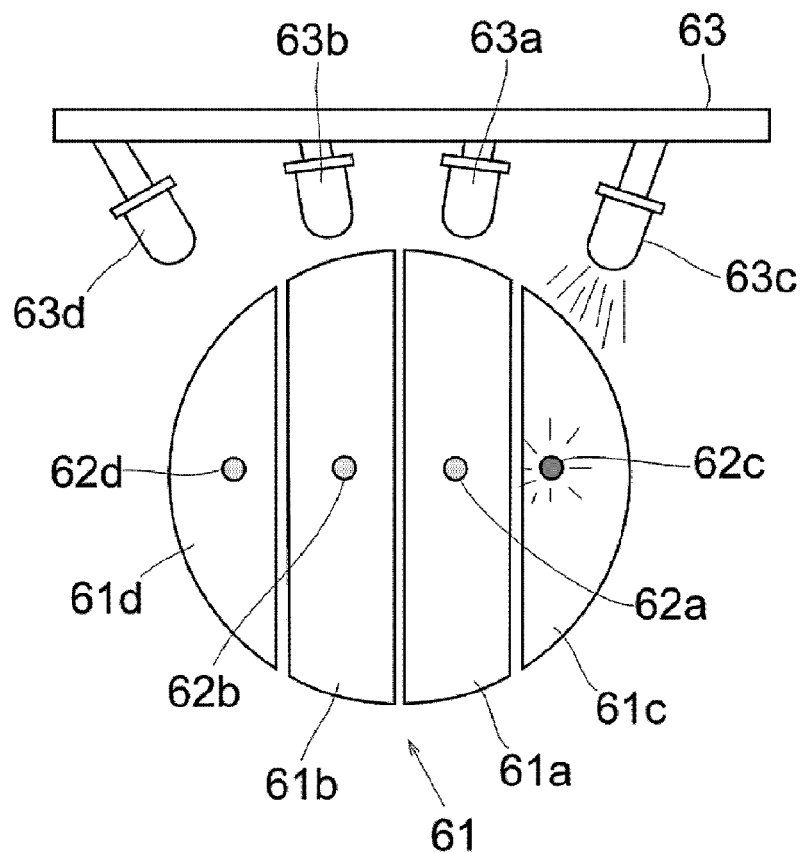
FIG. 9 is a front view of a target member and a target-illuminating light source according to a second embodiment of the present invention, as viewed from the subject's eye.

FIG. 9 is a front view of a target member and a target-illuminating light source used for anterior-ocular observation, which are included in the anterior-ocular observation optical system 11 according to a second exemplary embodiment of the present invention, as viewed from the subject's eye E. A target member 61 includes four transparent optical components 61$a$ to 61$d$ whose peripheral edges serve as scattering surfaces. The optical components 61$a$ to 61$d$ respectively have fixation targets 62$a$ to 62$d$ used for anterior-ocular observation. Similar to the first embodiment, the fixation targets 62$a$ to 62$d$ are each formed by eroding a section of the corresponding optical component into a predetermined target shape with an agent and then filling the eroded section with a white coating material, which serves as a scattering material.

Furthermore, similar to the first embodiment, the target member 61 is provided with a target-illuminating light source 63 configured to illuminate the optical components 61$a$ to 61$d$. The target-illuminating light source 63 has LEDs 63$a$ to 63$d$ configured to illuminate the fixation targets 62$a$ to 62$d$, respectively. The fixation targets 62$a$ to 62$d$ are disposed at positions where they are in a substantially conjugate relationship with the fundus Er of the subject's eye E with respect to the objective lens 2 and the lens 41. The target-illuminating light source 63 is connected to an output of the fixation-target light-source controller 32 which selectively turns on the LEDs 63$a$ to 63$d$.

Figure 10:
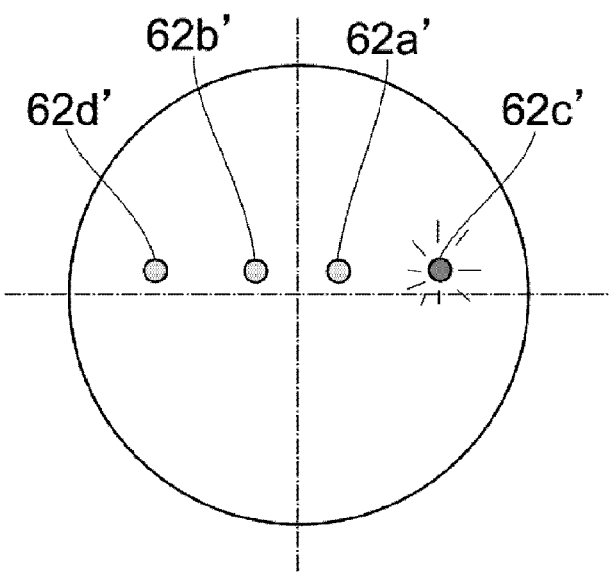
FIG. 10 is a front view of fixation-target images for anterior-ocular-observation observed by the subject's eye.
Figure 11:
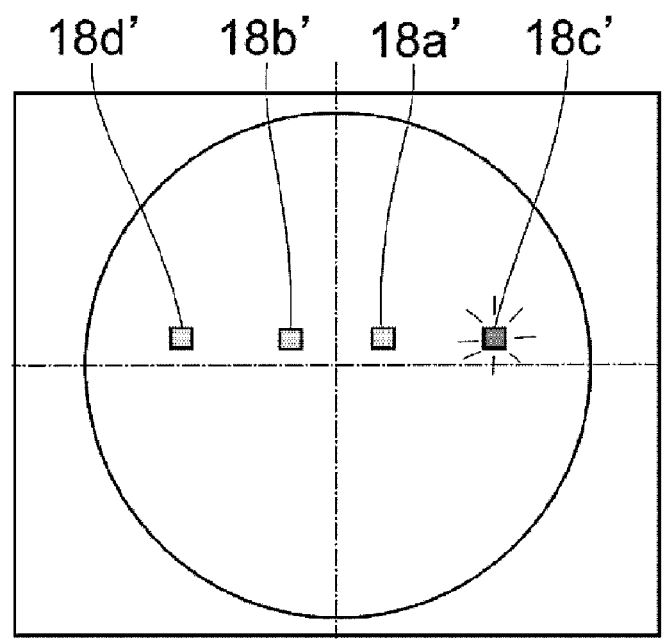
FIG. 11 is a front view of fixation-target images for fundus observation observed by the subject's eye.

FIG. 10 is a front view of fixation-target images 62$a$' to 62$d$' which are images of the respective fixation targets 62$a$ to 62$d$ observed by the subject's eye E. As shown in FIG. 10, the fixation-target images 62$a$' to 62$d$' for anterior-ocular observation are projected onto positions that do not coincide with the center of the observation light path. In correspondence to the fixation targets 62$a$ to 62$d$, the fixation target member 18 is similarly provided with four fixation targets 18$a$ to 18$d$ for fundus observation. FIG. 11 is a front view of fixation-target images 18$a$' to 18$d$' which are images of the fixation targets 18$a$ to 18$d$ of the fixation target member 18 observed by the subject. As shown in FIG. 11, the fixation-target images 18$a$' to 18$d$' are projected onto positions that do not coincide with the center of the observation light path. As shown in FIGS. 10 and 11, the fixation targets 18$a$ to 18$d$ can be projected on the fundus Er of the subject's eye E at the same positions as the fixation targets 62$a$ to 62$d$ for anterior-ocular-observation, respectively.

The fixation-target images 62$a$', 62$b$', 62$c$', 62$d$' and the respective fixation-target images 18$a$', 18$b$', 18$c$', 18$d$' are projected in the same visual line direction as viewed from the subject's eye E.

Figure 8:
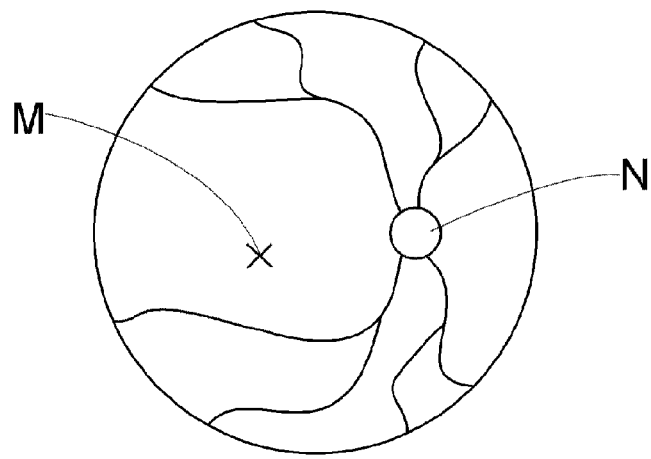
FIG. 8 illustrates a fundus image in which an optic disc and a macula lutea are evenly disposed.
Figure 12:
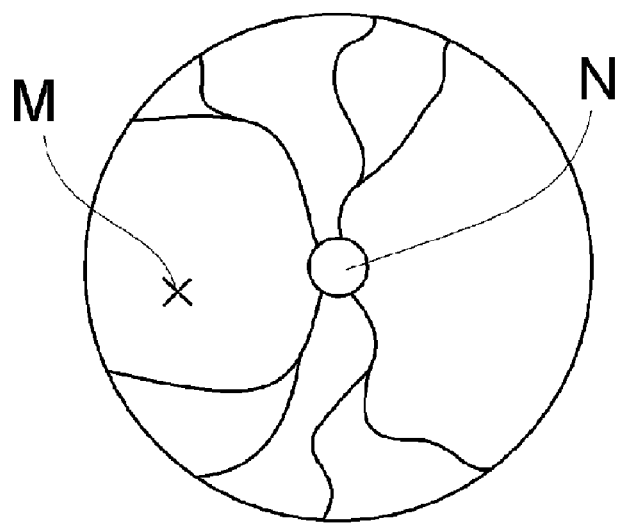
FIG. 12 illustrates a fundus image having an optic disc disposed in the center.

When the right eye is fixed on the fixation-target image 62$a$' and the fixation-target image 18$a$', these images are projected to a position where a fundus image as shown in FIG. 8 is attained, which has evenly-disposed optic disc N and macula lutea M and is suitable for a screening test, such as a complete physical examination and a mass health examination. On the other hand, when the right eye is fixed on the fixation-target image 62c' and the fixation-target image 18c', these images are projected to a position where a fundus image as shown in FIG. 12 is attained, which has the optic disc N in the center and is thus suitable for a screening test for glaucoma.

When the left eye is fixed on the fixation-target image 62b' and the fixation-target image 18b', these images are projected to a position where a fundus image having evenly-disposed optic disc N and macula lutea M and thus suitable for a screening test, such as a complete physical examination and a mass health examination, can be attained. When the left eye is fixed on the fixation-target image 62d' and the fixation-target image 18d', these images are projected to a position where a fundus image having the optic disc N in the center and thus suitable for a screening test for glaucoma can be attained.

Furthermore, in the fundus camera according to the present embodiment, the controller 26 is provided with an image-pickup-area selecting switch for selecting between two modes, which are a mode for picking up the fundus image having the evenly-disposed optic disc N and macula lutea M and a mode for picking up the fundus image having the optic disc N in the center. This switch is connected to the controller 26 of the fundus camera shown in FIG. 1.

For example, when the apparatus is set to correspond to the subject's right eye E, the examiner may use the image-pickup-area selecting switch to select the mode for picking up the fundus image having the optic disc N in the center. In response to this selection, the controller 26 determines that the subject's eye E detected by the left/right eye detector 31 is the right eye. The controller 26 controls the fixation-target light-source controller 32 so as to turn on the LED 63c that illuminates the fixation target 62c for anterior-ocular observation. As a result, the fixation target 62c is projected onto the subject's eye E.

Referring to FIG. 10, the subject's eye's E gaze is fixed at the fixation-target image 62c', which is the image of the fixation target 62c illuminated by the LED 63c, whereby the visual line is stabilized. Similar to the first embodiment, the examiner can complete the rough positioning process between the subject's eye E and the fundus camera while observing the anterior ocular segment Ep. In that case, the positioning process can readily be performed since the visual line of the subject's eye E is stable.

Subsequently, the examiner can operate the observation-area selecting switch 29 so as to switch to the fundus observation mode. The controller 26 then removes the anterior-ocular observation optical system 11 from the light axis L3. In addition, based on the detection result of the left/right eye detector 31, the controller 26 controls the controller 33 so as to drive the liquid crystal display panel and the backlight of the fixation target member 18 for fundus observation. A light beam from the observation fixation target member 18 reaches the fundus Er of the subject's eye E in the same manner as in the first embodiment. In this case, the left/right eye detector 31 detects that the subject's eye E is a right eye, and the mode for picking up the fundus image having the optic disc N in the center can be selected using the image-pickup-area selecting switch.

Consequently, the image of the fixation target 18c projected on the fundus Er as shown in FIG. 11 is projected on the subject's eye E as a fixation-target image 18c', and the subject's eye's E gaze is fixed at the fixation-target image 18c', whereby the visual line is stabilized. Similar to the first embodiment, the captured still image of the fundus is stored in the image memory 27.

Accordingly, the fixation-target image 62c' and the fixation-target image 18c' are projected in the same visual line direction as viewed from the subject's eye E, such that these images are projected to a position where a fundus image having the optic disc N in the center can be attained when viewed through the right eye. Subsequently, the observation-area selecting switch 29 can be operated to remove the anterior-ocular observation optical system 11 from the light axis L3, thereby switching the observation area from the anterior ocular segment Ep to the fundus Er. Even in this case, the visual line remains stable without the subject's eye E losing sight of the fixation target.

Consequently, it is not necessary to adjust the positioning and to perform the fixation guiding operation again, thereby contributing to a shorter imaging time and less complexity and trouble in the overall operation. In addition, the fixation targets corresponding to the left and right eyes can be selectively projected to positions where the optic discs and the macula luteas are evenly disposed or to positions where the optic discs are in the center.

Accordingly, a fundus image suitable for a screening test, such as a complete physical examination and a mass health examination, or for a screening test for glaucoma can be efficiently attained.

Furthermore, in the first and second embodiments, when picking up a fundus image of a desired area other than the fundus image having the evenly disposed optic disc N and macula lutea M and the fundus image having the optic disc N in the center, the fixation of the subject's eye may be guided as follows. First, the fixation-target images 51a', 51b' or the fixation-target images 62a' to 62d' are projected. Subsequently, upon switching from the anterior-ocular observation mode to the fundus observation mode, the fixation-target images 18a' to 18d' of the fixation target member 18 for fundus observation are projected once onto substantially the same optical positions as the previously selected and projected fixation-target images. The fixation target member 18 may then be shifted to a position where a fundus image of the desired area can be attained.

Although the first and second embodiments of the present invention have been described above, the technical scope of the present invention is not limited to the above embodiments, and modifications are permissible within the scope and spirit of the present invention. Furthermore, in addition to fundus cameras, the present invention is also applicable to other types of ophthalmic apparatuses, such as tonometers, refractometers, and keratometers. According to the ophthalmic apparatus in each of the above embodiments, when the observation mode is switched from the anterior-ocular observation mode to the fundus observation mode, a fixation target for fundus observation can be projected onto the same position as the fixation target for anterior-ocular observation, as viewed from the subject's eye. Thus, the visual line remains stable without the subject's eye losing sight of the fixation target. Accordingly, it is not necessary to adjust the positioning and to perform the fixation guide operation again, thereby contributing to a shorter imaging time and less complexity and trouble in the overall operation.

In addition, the fixation targets for anterior-ocular-observation corresponding to the left and right eyes can be selectively projected to positions where the optic discs and the macula luteas are evenly disposed or to positions where the optic discs are in the center. Accordingly, a fundus image suitable for a screening test, such as a complete physical examination and a mass health examination, or for a screening test for glaucoma can be efficiently attained.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese hereby incorporated by reference herein in its entirety.

What is claimed is:

1. An ophthalmic apparatus comprising:
   a first optical system for observing a subject's illuminated eye;
   a second optical system for changing an observation area through the first optical system, the second optical system being moved into a light path of the first optical system when an anterior-ocular image of the subject's eye is to be observed, the second optical system being removed from the light path of the first optical system when a fundus of the subject's eye is to be observed;
   a first fixation-target projecting unit for anterior-ocular observation disposed within the second optical system and configured to project fixation targets for anterior-ocular observation onto the subject's eye at positions not coinciding with a center of the light path;
   a second fixation-target projecting unit for fundus observation configured to project fixation targets for fundus observation onto the subject's eye; and
   a controller that allows the second fixation-target projecting unit to project the fixation targets for fundus observation onto predetermined positions on the subject's eye when the second optical system is removed, said predetermined positions corresponding to the positions to which the fixation targets for anterior-ocular observation are projected.

2. The ophthalmic apparatus according to claim 1, further comprising:
   a left/right eye detecting unit configured to detect whether the subject's eye is a left eye or a right eye,
   wherein, based on the detection result of the left/right eye detecting unit, the controller selects a position for projecting one of the fixation targets for anterior-ocular observation onto the subject's eye from said positions to which the fixation targets for anterior-ocular observation are projected.

* * * * *